United States Patent
Messmer

(10) Patent No.: US 8,840,631 B2
(45) Date of Patent: Sep. 23, 2014

(54) COMPARTMENT SYNDROME TREATMENT METHOD AND SURGICAL INSTRUMENT FOR SAME

(75) Inventor: Sarah Messmer, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 96 days.

(21) Appl. No.: 13/391,451

(22) PCT Filed: Sep. 28, 2010

(86) PCT No.: PCT/US2010/050473
§ 371 (c)(1),
(2), (4) Date: Feb. 21, 2012

(87) PCT Pub. No.: WO2011/053422
PCT Pub. Date: May 5, 2011

(65) Prior Publication Data
US 2012/0150208 A1    Jun. 14, 2012

Related U.S. Application Data

(60) Provisional application No. 61/255,987, filed on Oct. 29, 2009.

(51) Int. Cl.
*A61B 17/32* (2006.01)

(52) U.S. Cl.
USPC ............................................ 606/170; 606/167

(58) Field of Classification Search
USPC ......... 606/135, 137, 138, 159, 167, 170, 171; 600/183; 30/289, 294, 244–246
See application file for complete search history.

(56) References Cited

U.S. PATENT DOCUMENTS

| | | | | |
|---|---|---|---|---|
| 2,691,370 A | * | 10/1954 | Wallace | 600/104 |
| 4,963,147 A | * | 10/1990 | Agee et al. | 606/170 |
| 5,053,044 A | | 10/1991 | Mueller et al. | |
| 5,112,346 A | * | 5/1992 | Hiltebrandt et al. | 606/170 |
| 5,578,051 A | | 11/1996 | Mirza | |
| 5,584,842 A | * | 12/1996 | Fogarty et al. | 606/159 |
| 5,620,446 A | | 4/1997 | McNamara et al. | |
| 5,720,754 A | | 2/1998 | Middleman et al. | |
| 5,797,906 A | | 8/1998 | Rhum et al. | |
| 6,051,005 A | | 4/2000 | Brandsey et al. | |

(Continued)

FOREIGN PATENT DOCUMENTS

| | | |
|---|---|---|
| DE | 4140402 | 7/1991 |
| WO | 96/37157 | 11/1996 |
| WO | 2008/028701 | 3/2008 |

*Primary Examiner* — David Eastwood
(74) *Attorney, Agent, or Firm* — Liell & McNeil

(57) ABSTRACT

A subcutaneous fasciotomy is performed to relieve pressure due to compartment syndrome. A small incision is made in a patient's skin. A surgical instrument is advanced through the entry location, and moved between the skin and the fascia of the patient to a remote location, with a cutter of the instrument in a stowed configuration. After reaching the remote location, the cutter is deployed to pierce an initial opening in the fascia at the remote location. The fascia is maintained adjacent a blade of the cutter via a notch shape that traps the fascia. The instrument is then withdrawn back toward the entry location with the blade incising the fascia to relieve pressure in the muscle compartment. The surgical instrument is then removed through the entry incision.

5 Claims, 3 Drawing Sheets

(56) References Cited

U.S. PATENT DOCUMENTS

| | | |
|---|---|---|
| 2004/0098005 A1 | 5/2004 | Mirza et al. |
| 2005/0137448 A1* | 6/2005 | Wingler et al. .............. 600/34 |
| 2005/0251161 A1 | 11/2005 | Saadat et al. |
| 2006/0241665 A1 | 10/2006 | Bosley et al. |
| 2007/0225740 A1* | 9/2007 | Suddaby ................. 606/170 |
| 2008/0221579 A1* | 9/2008 | Panchbahavi ............. 606/79 |
| 2009/0182192 A1* | 7/2009 | Shiono et al. ............ 600/103 |
| 2009/0187203 A1* | 7/2009 | Corvi et al. .............. 606/159 |

* cited by examiner

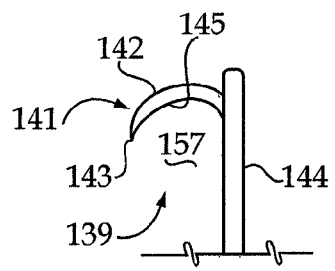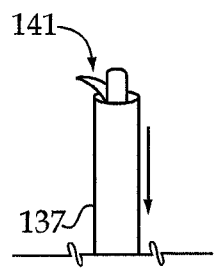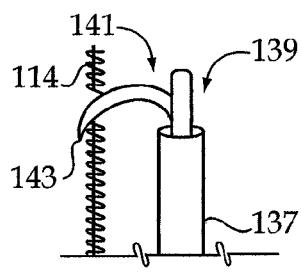
Figure 10a     Figure 10b     Figure 10c
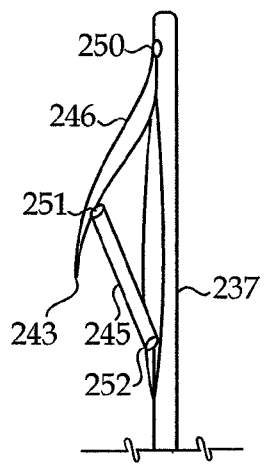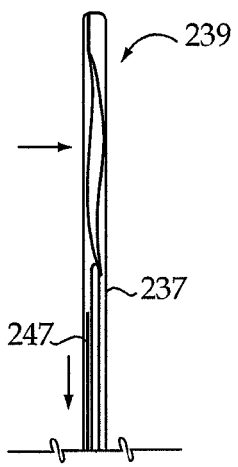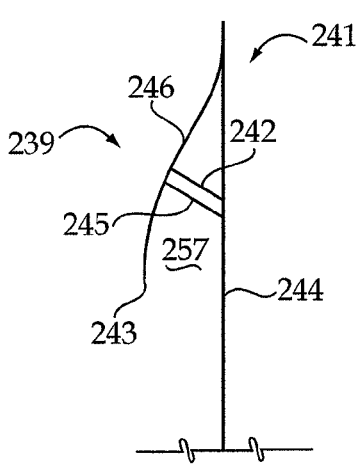
Figure 11a     Figure 11b     Figure 11c
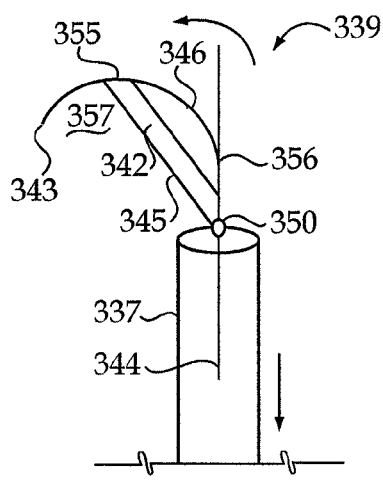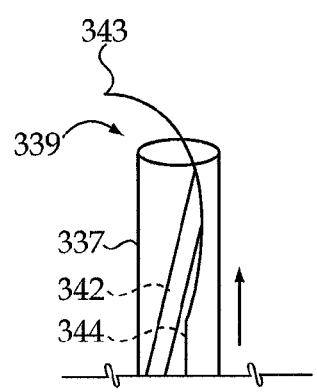
Figure 12a     Figure 12b

_US 8,840,631 B2_

COMPARTMENT SYNDROME TREATMENT METHOD AND SURGICAL INSTRUMENT FOR SAME

TECHNICAL FIELD

The present disclosure relates generally to medical devices, and more particularly to a surgical instrument for treating compartment syndrome.

BACKGROUND

The muscle groups of the arms and legs are enclosed in a thick tissue called fascia that does not readily expand. Fascia creates individual compartments for the muscle groups by attaching to the bone, encircling the muscle and reattaching to the bone on the other side. Compartment syndrome is defined as a condition in which increased pressure within the confined space defined by the fascia compromises tissue circulation and inhibits muscular function. High pressure within the fascia compartment may be due to swelling and contracting of the muscles, or from excess bleeding after surgery or trauma, and other causes known in the art. Compartment syndrome generally refers to high pressure conditions within the fascia compartment that rise to a level requiring surgical treatment to relieve the pressure. Without relieving the pressure, the tissues within the fascia compartment can be deprived of oxygen, which can cause damage to blood vessels, nerves and muscle cells. Without treatment to relieve the pressure, compartment syndrome can lead to paralysis, loss of limb or even death.

One currently accepted procedure that is commonly used to treat compartment syndrome is fasciotomy, or cutting of the fascia to relieve the pressure. In a typical procedure, the physician cuts through the skin, and spreads the skin apart to reveal the fascial layer over the length of the compartment. Next, the fascial layer is cut in order to relieve the pressure. In most instances, the wound is left open until the swelling recedes, and then the skin is sewn up to close the wound. In some instances, a skin graft may be used to cover the opening. The cut through the fascia may be made with scissors in full view of the physician performing the procedure. Because the wound may be left open while waiting for the swelling to go down, the procedure can cause great stress on the patient, as well as create a substantially increased risk of infection. Although the open wound technique remains the most practiced treatment for compartment syndrome, more recently, an endoscopically assisted fasciotomy treatment has been proposed. While under endoscopic visualization, scissors are used to cut the fascia.

The present disclosure is directed to one or more of the problems associated with current treatment strategies for compartment syndrome.

SUMMARY

In one aspect, a method of treating compartment syndrome includes moving a cutter of an instrument from an entry location to a remote location within a patient, while the cutter of the instrument is in a stowed configuration. The cutter of the instrument is deployed from the stowed configuration to a deployed configuration at the remote location. The muscle compartment fascia is incised by piercing the muscle compartment fascia with a pointed tip of the cutter followed by moving a blade of the cutter from the remote location toward the entry location.

In another aspect, a surgical instrument includes a rod extending between a handle and a cutter, which includes a blade and a pointed tip. The cutter is moveable with respect to the rod between a stowed configuration and a deployed configuration. A notch is defined at least in part by the blade, when the cutter is in the deployed configuration. The pointed tip and one end of the blade are closer to the rod in the stowed configuration than in the deployed configuration. A segment of the rod is slidably positioned within a sheath.

BRIEF DESCRIPTION OF THE DRAWINGS

FIGS. 10a-c are side views of a cutter of a surgical instrument assembly according to another embodiment of the present disclosure;

FIGS. 11a-c are different views of a cutter of still another embodiment of a surgical instrument assembly according to the present disclosure; and FIGS. 12a-b are side views of a cutter of a surgical instrument assembly according to still another embodiment of the present disclosure.

DETAILED DESCRIPTION

Figure 1:
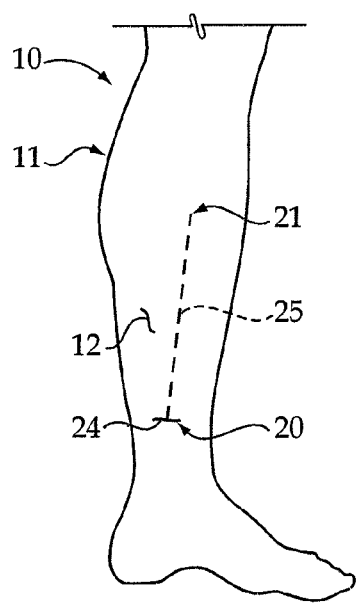
FIG. 1 is a side view of a patient's leg with markings to indicate a fasciotomy according to the present disclosure.
Figure 2:
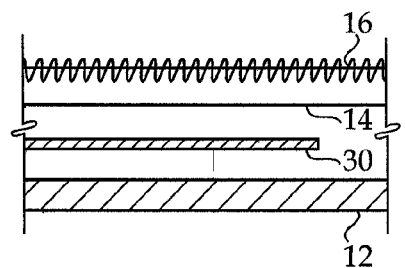
FIG. 2 is a partial sectioned side view through the patient's leg showing an initial wire guide step for performing a fasciotomy according to the present disclosure.

Referring to FIG. 1, the lower leg 11 of a patient 10 is shown with markings to indicate a fasciotomy treatment for compartment syndrome of a calf muscle according to the present disclosure. The procedure may be performed by making a small incision 24 at an entry location 20 through the patient's skin 12. A surgical instrument assembly, described infra, may be moved through incision 24 and under the patient's skin 12 to arrive at a remote location 21. A cutter of the surgical instrument assembly is maintained in a stowed configuration when being moved from entry location 20 to remote location 21. Those skilled in the art will appreciate that entry location 20 is chosen to be located near one end of a desired fasciotomy incision. The remote location 21 may be chosen corresponding to the opposite end of the fasciotomy incision. The remote location 21 and entry location 20 may be reversed as desired by the physician performing the fasciotomy. In addition, the distance between entry location 20 and remote location 21 may roughly correspond to the desired fasciotomy incision length to relieve pressure from the underlying muscle compartment. After reaching the remote location 21, the surgical instrument assembly according to the present disclosure is changed from its stowed configuration to its deployed configuration. When this occurs, a pointed tip of a cutter of the instrument pierces the fascia at remote location 21. Next, the surgical instrument assembly is withdrawn in the direction of entry location 20 with the blade of the cutter of the surgical instrument incising the fascia along incision 25. As used in this disclosure, the verb incise means to cut in a manner other than scissoring. After incision 25 is complete, the surgical instrument assembly is withdrawn from the patient through entry incision 24. The entry incision 24 may then be closed or dressed as required by the attending physician.

Figure 5:
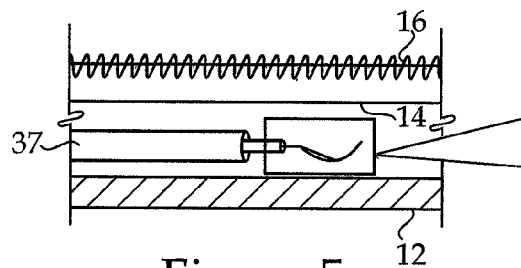
FIG. 5 is a view similar to that of FIG. 4 with the surgical instrument being moved from its completely stowed configuration of FIG. 4 to a partially deployed configuration.
Figure 5A:
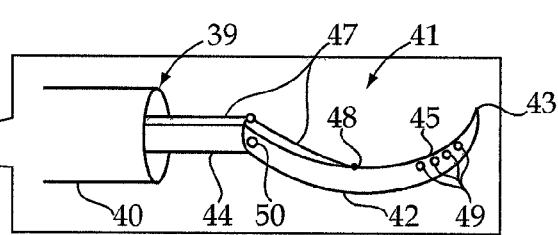
FIG. 5a is an enlarged view of the cutter portion of the surgical instrument shown in FIG. 5.
Figure 6:
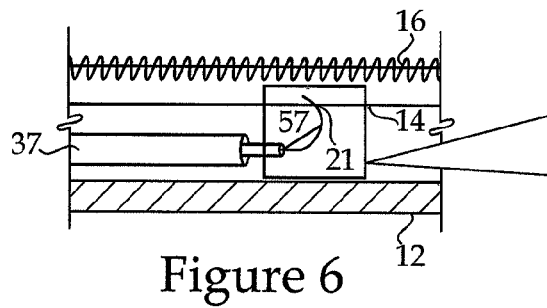
FIG. 6 is a view similar to that of FIG. 5 except with the cutter of the surgical instrument in its deployed configuration.
Figure 6A:
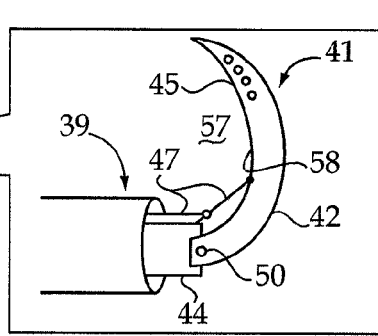
FIG. 6a is an enlarged view of the cutter of the surgical instrument of FIG. 6.
Figure 6B:
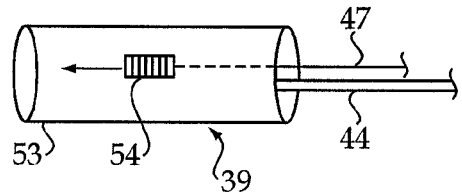
FIG. 6b is an enlarged view of the handle portion of the surgical instrument showing how the cutter may be moved from a stowed configuration to a deployed configuration.

Referring now to FIGS. 5-6b, a surgical instrument assembly 39 according to one embodiment of the present disclosure is illustrated. In general, surgical instrument assembly 39 includes a rod 44 defining a longitudinal axis and extending between a handle 53 and a cutter 41. A proximal end of rod 44 is coupled to handle 53, while a distal end is pivotably connected to cutter 41. The cutter 41 includes a blade 42 extending axially outward of a distal end of rod 44, and a pointed tip 43, which in this embodiment is located at one end of blade 42. The term "pointed tip" means a protuberance that is sufficiently sharp to pierce fascia. Blade 42 includes a cutting edge 45 that has an arcuate shape that defines a notch 57. Notch 57 may be defined at least in part by blade 42, when the cutter is in a deployed configuration as shown in FIG. 6a. FIG. 5a shows cutter 41 in a stowed configuration. In this embodiment, a deployment wire 47 is attached at one end to blade 42 at attachment point 48, and at its other end to a button 54 slidably attached to the handle 53 as shown in FIG. 6b. The blade 42 is attached to rod 44 via a hinge 50, such that movement of button 54 in the proximal direction as shown in FIG. 6b causes blade 42 to pivot about hinge 50 to move cutter 41 from the stowed configuration as shown in FIG. 5a to the deployed configuration as shown in FIG. 6a, and advancing pointed tip 43 closer to the proximal end of rod 44. Attachment point 48 is shown to be distal to hinge 50 in FIGS. 5a and 6a. In this embodiment, the vertex 58 of notch 57 is defined by blade 42, so that when the fascia is trapped in notch 57, the fascia is urged toward vertex 58 to make stable blind incising of the fascia possible. The blade 42, or other portion of surgical instrument assembly 39, may include ultrasound reflecting dimples 49 or another suitable feature so that ultrasound imaging or another imaging technology can be utilized during the treatment procedure. For instance, ultrasound imaging may be utilized to confirm an appropriate location and/or orientation of cutter 41 when being moved from its stowed configuration to its deployed configuration, and also may be useful during the fascia incising step itself. Surgical instrument assembly 39 may also include a sheath 40 within which rod 44 slides and cutter 41 may be withdrawn when in its stowed configuration to avoid interaction between cutting edge 45 and the patient's tissue while the instrument assembly 39 is being maneuvered from entry location 20 to remote location 21. Movement of handle 53 relative sheath 40 is communicated to cutter 41 via sliding of a segment of rod 44 within sheath 40.

FIGS. 10a-10c show a surgical instrument assembly according to an alternative embodiment of the present disclosure. Instrument assembly 139 differs from that previously described in that the blade 142 deforms and straightens when withdrawn into sheath 137 to assume its stowed configuration as shown in FIG. 10b. When rod 144 is moved in the distal direction relative to sheath 137, the pointed tip 143 of blade 142 emerges from sheath 137 to pierce an initial opening in fascia 114 as shown in FIG. 10c. When fully deployed as shown in FIG. 10a, the blade 142 defines a notch 157 within which the fascia may be trapped. When the surgical instrument assembly 139 is withdrawn, the cutter 141 remains in a deployed configuration as shown in FIG. 10a resulting in an incising of fascia 114, such as that suggested in FIG. 1. Blade 142, in this embodiment may be made in a hook shape out of a suitable highly flexible material, such as nitinol, and include a cutting edge 145 that defines notch 157. Also, blade 142 might be sufficiently flexible that it can be straightened for positioning in a stowed configuration within a sheath 137 as shown in FIG. 10b, but be sufficiently rigid during its deployment and in its deployed configuration that cutter 141 can pierce an initial opening in the fascia 114 as shown in FIG. 10c, and maintain cutting edge 145 sufficiently stiff to perform the incision in a deployed configuration as shown in FIG. 10a. Blade 142 may be attachment to rod 144 in any suitable manner, such as via a weld or maybe even a living hinge strategy.

Referring now to FIGS. 11a-c, a surgical instrument assembly 239 according to still another embodiment of the present disclosure has a configuration and deployment action that resembles a Park Blade Septostomy Catheter of a type manufactured by Cook, Inc. and sometimes used in interventional cardiology procedures. In particular, a relatively rigid rod 244, which also functions as a deployment wire 247, slides within a sheath 237. A blade 242 is attached to one end of deployment wire 247 at a hinge 252, and attached at its opposite end to a puncturing component 246 via a hinge 251. Piercing component 246 includes a pointed tip 43 at one end, and is attached at its opposite end to sheath 237 via a hinge 250. Those skilled in the art will appreciate that a hinge according to the present disclosure can include conventional pinned mechanical hinges, living hinges which rely simply upon a bending of a unitary piece of material, or even a deformation process associated with highly flexible materials such as nitinol. When the deployment wire 247 is pulled in a proximal direction, the surgical instrument assembly 239 assumes a stowed configuration as shown in FIG. 11b, with puncturing component 246 drawn closer to a portion of sheath 237 covering the cutting edge 245 of blade 242. In other words, the cutting edge 245 is arranged in parallel with the axis defined by deployment wire 247, which slides within sheath 237. When the deployment wire 247 is moved in the distal direction, the blade 242 pivots about hinges 251 and 252 along with puncturing component 246 rotating about hinge 250 to move the surgical instrument assembly 239 to its deployed configuration as shown in FIGS. 11a and 11c. The pointed tip 243 may be oriented such that it may pierce the fascia during the deployment maneuver like the previous embodiments, or it may pierce the fascia as the surgical instrument assembly 239 is withdrawn in the proximal direction. After being pierced, the fascia may become trapped in notch 257, which is defined partly by blade 242, to perform the remaining steps of the fascia incising procedure.

Referring now to FIGS. 12a and 12b, a surgical instrument assembly 339 according to still another embodiment of the present disclosure is illustrated. This embodiment differs from the earlier embodiments in that a flexible hook portion 346 is attached at one end to a relatively rigid rod 344, such as via a solder joint at attachment point 357. Flexible hook portion includes a pointed tip 343 at its opposite end that facilitates in making an initial entry opening into the fascia to be incised. A blade 342 has one end attached to an intermediate portion of hook 346 at attachment point 355, and attached at its opposite end via a hinge 350 to rod 344. Together, hook portion 346 and cutting edge 345 of blade 342 define a notch 357 that receives and traps the fascia to be cut in a manner similar to that described previously. When the rod 344 is retraced in the proximal direction into a sheath 337, the cutter 341 deforms into the lumen of sheath 337 into a stowed configuration as shown in FIG. 12b. As with the previous embodiment, it is contemplated that the pointed tip 343 may pierce an initial opening into the fascia during the deployment procedure from the stowed configuration as shown in 12b to the deployed configuration as shown in 12a. Thereafter, the instrument assembly 339 is withdrawn in the proximal direction with the fascia trapped in notch 357 adjacent cutting edge 345 to perform the incising step of the compartment syndrome treatment procedure according to the present disclosure.

INDUSTRIAL APPLICABILITY

Referring now to FIGS. 1-9, the various steps of treating compartment syndrome according to an aspect of the present disclosure are illustrated in a stepwise manner. The procedure is initiated by making a relatively short skin incision 24 at an entry location 20 through the patient's skin 12 adjacent the muscle to be treated. Nevertheless, those skilled in the art will appreciate that, depending upon circumstances, entry into the patient's body may be gained through a natural opening, through an existing wound or via any other manner known in the art. Thus, the entry location 20 may not always correspond to the end point for the desired fasciotomy incision 25. After the small skin incision 24 is made, a dilator may or may not be used to enlarge the opening. Next, a wire guide may be advanced into the patient between skin 12 and fascia 14 over the muscle 16, which is currently experiencing high pressure within the compartment defined by the fascia. The wire guide 30 may have sufficient rigidity that it can be advanced through the patient's tissue without buckling or kinking, but retains sufficient flexibility that the physician can maneuver the wire guide from the entry location 22 toward the remote location 21 without utilizing a pre-existing body passageway, such as that associated with minimally invasive cardiology procedures known in the art. Ultrasound imaging or other strategies known in the art may be utilized to confirm that the end of the wire 30 is at the desired remote location 21 corresponding to the desired starting point for fascia incision 25. Alternatively, the initial incision 24 may be made not only through the patient's skin 12 but also through the fascia 14 such that the wire guide is advanced in the area between fascia 14 and the muscle 16, without departing from the present disclosure.

Figure 3:
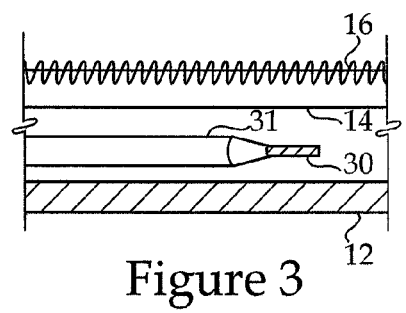
FIG. 3 is a view similar to that of FIG. 2 after a tapered catheter has been advanced over the wire guide.
Figure 4:
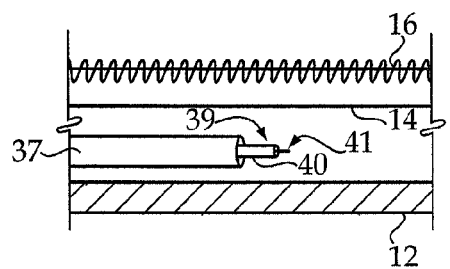
FIG. 4 is a view similar to that of FIG. 3 except after a sheath has been advanced over the tapered catheter and wire guide, which have been removed in favor of a surgical instrument advanced into the sheath according to the present disclosure.

Referring now to FIG. 3, after the wire guide 30 has been positioned as desired, a tapered catheter 31 may be advanced over the wire guide. Next, a sheath 37 may be advanced over the combined wire guide 30 and tapered catheter 31 as best shown in FIG. 4. The end of sheath 37 may now be located at or near the remote location 21. At this point, the tapered catheter 31 and wire guide 30 may be withdrawn. Next, the surgical instrument assembly 39, which includes its own sheath 40, is advanced through larger sheath 37 while the cutter 41 of the instrument remains in its stowed configuration as shown in FIG. 4. Those skilled in the art will recognize that one end of blade 42 and pointed tip 43 are closer to rod 44 in the stowed configuration thus in the deployed configuration. This is also true for the other embodiments. In the illustrated embodiment as shown in FIGS. 5 and 5a, the cutter 41 may be advanced out the end of sheath 40 either by moving rod 44 in the distal direction, or by moving sheath 40 in the proximal direction, or by a combination of both. At some point(s) or intermittently, it may be desirable to utilize ultrasound imaging or another technique to confirm the orientation of blade 42 so that the pointed tip 43 is pointed generally in the direction of the fascia 14. A proper orientation may ensure that, when cutter 41 is moved from its stowed configuration as shown in FIG. 5a to its deployed configuration as shown in 6a, the pointed tip may pierce through to make an initial opening in fascia 14 as shown in FIG. 6. Those skilled in the art will appreciate that the same procedure might also be utilized with the surgical instrument assembly positioned at the remote location 21 between fascia 14 and muscle 16 so that the piercing through fascia 14 occurs in the direction of the skin rather than in the direction of the muscle as shown in FIG. 6. Such an alternative is also contemplated within the scope of the present disclosure. After the fascia has been initially pierced by the pointed tip 43, the fascia 14 then becomes trapped in the notch 57 defined by cutter 41. With the notch 57 appropriately shaped, the fascia will be stably urged toward the vertex 58 of the notch 57 so that the incising procedure can be performed relatively blind. If necessary or desired, imaging may require that the rod 44 be rotated to reorient blade 42 properly with regard to fascia 14 before the deployment procedure is executed. In the event that the deployment procedure fails to gain an initial opening into fascia 14, the cutter 41 may be returned to its stowed configuration and the deployment procedure retried after reorienting instrument 39 to better position blade 42 in the proper orientation with regard to fascia 14.

Figure 7:
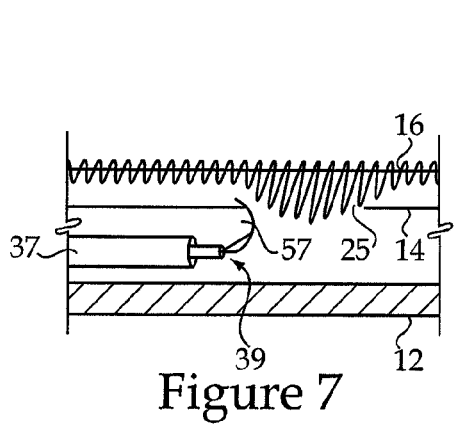
FIG. 7 is a view similar to that of FIG. 6 showing a fasciotomy partially completed.
Figure 8:
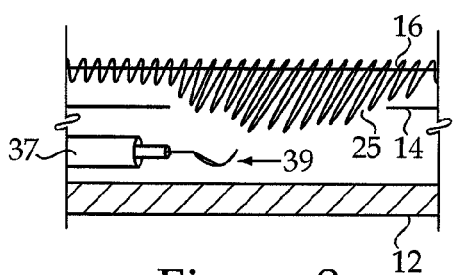
FIG. 8 is a view similar to that of FIG. 7 after the fasciotomy has been completed and the cutter of the surgical instrument is being moved toward its stowed configuration.
Figure 8A:
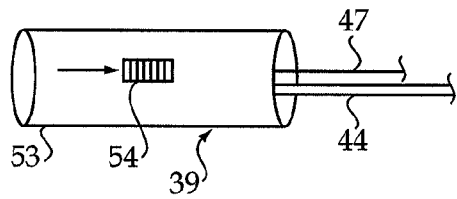
FIG. 8a is an enlarged view of the handle similar to that of the FIG. 6b showing how the cutter of the surgical instrument may be moved from its deployed configuration to its stowed configuration.
Figure 9:
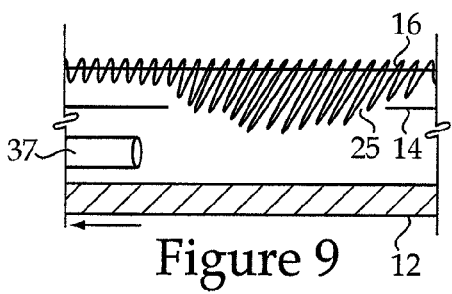
FIG. 9 shows a view similar to that of FIG. 8 where the surgical instrument assembly is being removed from the patient.

Referring now to FIG. 7, after an initial opening into fascia 14 has been gained, the surgical instrument assembly 39 is withdrawn in the proximal direction with sheath 37 sliding in the area between uncut skin 12 and uncut fascia 14 while the cutting edge 45 incises the fascia along incision line 25 to relieve pressure in muscle 16. After reaching the desired end of the long fascia incision 25, the surgical instrument assembly 39 may be reconfigured to its stowed configuration as shown in FIG. 8 by advancing button 54 in the distal direction. This causes deployment wire 47, which may have sufficient stiffness to avoid buckling, to pivot blade 42 about hinge 50 back to its stowed configuration as shown in FIGS. 5a and 8. Next, the sheath 44 may be advanced over blade 42 as shown in FIG. 9, and the entire surgical instrument assembly 39 along with sheath 37 may be then withdrawn from the patient through the skin incision opening 24. The relatively small skin incision opening 24 may then be closed in a suitable manner or covered with an appropriate dressing, as needed.

Those skilled in the art will appreciate that the above described procedure could be practiced with any of the disclosed surgical instrument assemblies without departing from the present disclosure. In addition, several of the described steps may possibly be eliminated under certain circumstances. For instance, the wire guide and tapered catheter steps may be eliminated from the procedure in some circumstances where the surgical instrument assembly itself is used as its own guide and is advanced through the small incision to reach the remote location to initiate the fascia incising procedure. Thus, in some instances it may also be possible to eliminate the large sheath 37, and the procedure performed without departing from the present disclosure. Finally, it may not be necessary and/or desirable to re-stow the cutter of the surgical instrument assembly after completing the fascia incision, but before the instrument assembly has been removed from the patient. In all versions of the surgical instrument assembly, a rod extends between a handle and a cutter, which includes a blade and a pointed tip. The cutter is moveable with respect to the rod between a stowed configuration and a deployed configuration. In addition, the blade defines at least a portion of a notch when the cutter is in a deployed configuration. Pointed tip and one end of the blade are positioned closer to the rod when in the stowed configuration than when in the deployed configuration. Finally, a segment of the rod is slidably positioned within a sheath.

Those skilled in the art will appreciate that the surgical instrument assemblies according to the present disclosure and the described treatment strategy allow a compartment syndrome fasciotomy procedure to be performed with a relatively small skin incision, but with a full length or long fascia incision. Furthermore, this may be done while reducing trauma to the patient, and in a manner that substantially reduces the risks of post operation infection often associated with the large gaping wounds of fasciotomies according to the prior art. Thus, one might expect a speedier recovery and no necessity for a possible skin graft to cover the wound.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A surgical instrument assembly comprising:
a rod extending between a handle and a cutter, which includes a blade and a pointed tip, and the rod defining a longitudinal axis;
the cutter being movable with respect to the rod between a stowed configuration and a deployed configuration;
a notch being defined at least in part by the blade, when the cutter is in the deployed configuration;
a segment of the rod being slidably positioned within a sheath, and the rod having a proximal end coupled to the handle and a distal end connected to the cutter such that movement of the handle relative the sheath is communicated to the cutter via the sliding of the segment of the rod;
a hinge pivotably connecting the rod to the blade and forming the connection of the rod to the cutter;
a cutter deployment wire external to and radially spaced from the rod, the cutter deployment wire attached at one end of the blade, and having a segment extending along the rod within the sheath; and
the cutter being in the stowed configuration within the sheath, and the blade extending axially outward from the distal end of the rod, such that an attachment point of the cutter deployment wire to the blade is distal to the hinge, and moving the cutter deployment wire in a proximal direction causes the cutter to pivot toward the deployed configuration and advances the pointed tip closer to the proximal end of the rod.

2. The instrument of claim 1, wherein a vertex of the notch is defined by the blade.

3. The instrument of claim 1, wherein the pointed tip is located at one end of the blade.

4. The instrument of claim 1, wherein the blade includes at least one ultrasound reflecting dimple.

5. The instrument of claim 4, wherein the blade is connected to the rod via a hinge;
a vertex of the notch is defined by the blade; and
the pointed tip is located at one end of the blade.

* * * * *